United States Patent [19]
Miller et al.

[11] Patent Number: 5,483,843
[45] Date of Patent: Jan. 16, 1996

[54] TRANSPORT APPARATUS

[75] Inventors: Leslie A. Miller, San Jose; Thomas J. McCall, Jr., Fremont; Samuel A. Marquiss, Santa Clara; Douglas H. Smith, Los Altos; Richard F. Johnson, San Jose, all of Calif.

[73] Assignee: Thermo Separation Products Inc., Fremont, Calif.

[21] Appl. No.: 891,869

[22] Filed: Jun. 1, 1992

[51] Int. Cl.$^6$ ................................................ G01N 35/00
[52] U.S. Cl. ................................ 73/864.23; 73/864.21; 422/63
[58] Field of Search ................................ 73/864.21, 864.23; 422/62, 64–68.1, 63

[56] References Cited

U.S. PATENT DOCUMENTS

| | | | |
|---|---|---|---|
| 4,478,095 | 10/1984 | Bradley et al. | 73/864.23 |
| 4,595,562 | 6/1986 | Liston et al. | 422/63 |
| 4,622,457 | 11/1986 | Bradley et al. | 73/864.21 |
| 4,713,218 | 12/1987 | Schwartz | 422/63 |
| 4,713,974 | 12/1987 | Stone | 73/864.23 |
| 4,944,781 | 7/1990 | Ruggirello | 73/23.41 |
| 4,951,512 | 8/1990 | Mazza et al. | 73/864.23 |
| 4,957,009 | 9/1990 | Nohl et al. | 73/864.84 |
| 4,969,993 | 11/1990 | Nash, Jr. et al. | 422/70 |
| 4,980,130 | 12/1990 | Metzger et al. | 73/863.71 |
| 5,055,263 | 10/1991 | Meltzer | 73/864.24 |
| 5,201,232 | 4/1993 | Uffenheimer | 73/864.23 |
| 5,282,978 | 2/1994 | Polk, Jr. et al. | 422/63 |

*Primary Examiner*—Richard E. Chilcot, Jr.
*Assistant Examiner*—George M. Dombroske
*Attorney, Agent, or Firm*—Killworth, Gottman, Hagan & Schaeff

[57] ABSTRACT

A vial transport apparatus which is capable of storing and retrieving samples and then transporting them from one location in a sampling system to another without the complexity and expense of robotic arms or gripper elements is provided. A passive hook arrangement is utilized to engage the vials for transport and can be operated using a standard three motor system for transport in the X, Y, and Z directions. The hook supports the vial from beneath and at least partially surrounds the vial to entrap it during transport thereof.

27 Claims, 7 Drawing Sheets

TRANSPORT APPARATUS

BACKGROUND OF THE INVENTION

This invention relates to the movement of vials or containers from one location to another by a transport mechanism. More particularly, the invention relates to the movement of liquid sample-containing vials in a chemical analysis system from a tray to one or more sample preparation and/or analysis stations.

Automation of chemical analyses which were once performed by hand has progressed significantly. In the field of liquid chromatography, a number of automated chromatographic analysis systems are currently commercially available. These systems, referred to as autosamplers, aid in the automation of chromatographic analysis by storing a number of individual samples and injecting them sequentially into a chromatograph for analysis. The chromatographic analysis, which typically takes between about 10 to 60 minutes, can be completed without human intervention.

Some early autosampler systems used circular trays having a single row of sample-containing vials about the periphery thereof. Typically, the vials are of a small (i.e., 1.8 ml) volume and fabricated of glass. The vials may be sealed with a rubber septum held onto the top of the vial by a cap with a hole in the center thereof. The hole exposes a portion of the rubber septum to a hollow needle which is pushed through the septum and into the sample.

The needle is used to withdraw a predetermined amount of the sample and then cause that sample to be injected into the chromatograph. In these early autosamplers, the tray holding the vials rotated to position succeeding vials beneath the needle. The needle was then lowered, sample removed, and the withdrawn. The withdrawn sample was then injected into the sample loop of an injection valve.

Autosampler systems of more recent vintage still perform the same basic tasks. However, demand has increased for systems which are capable of storing an increased number of sample vials in less space. The quality of chromatography columns has improved so that analysis time for an individual sample has decreased to 10 minutes or less. End users of the autosamplers desire a system which can be loaded with enough samples to run several hours, and preferably overnight, without further human intervention.

This has led to the development of several different tray configurations including smaller circular trays arranged on a planetary platter. Bradley et al, U.S. Pat. No. 4,622,457, shows this tray configuration. Other autosamplers use trays containing multiple rows of vials in a rectangular configuration. Most of these systems, however, still place the sample-containing vials in a stationary matrix and move a needle to the vial to be sampled. Thus, the typical autosampler includes three motors for movement of the needle in the X and Y directions, as well as the Z direction, for sample withdrawal.

Currently, additional demands are being placed on such autosampler systems to increase further the automation of the chemical analyses. In addition to automated sampling, there is the desire to produce systems capable of some sample preparation. For example, there may be a need to dilute the sample before analysis or to add a reagent to aid in sample detection. Some reagents may take several minutes to react and may require continuous mixing and/or heating at elevated temperatures. As this time is comparable to the time required for chromatographic analysis, it may be desirable to have more than one sample in process at one time.

Further, it may become necessary to remove a sample from the tray matrix and perform an operation on it such as mixing or heating. As it is difficult to control a system where more than one device moves over a stationary matrix of vials to perform simultaneous operations, and since some operations may be better performed by removal from the matrix, a system which has the capability to remove vials from a matrix and transport them to work stations where these sample-preparation operations may be performed has significant advantages over systems which are incapable of this function.

Commercial systems have been developed for sample preparation which have the capability of moving sample vials from location to location. Such systems use robotic arms to grasp the vials and move them. However, the need for a gripping capability requires the addition of yet another motor which actuates the gripping mechanism in the system. This adds to the cost and complexity of such systems. Accordingly, there is a need in the art for an autosampler which is capable of removing sample-containing vials from a matrix and transporting the vials from one location to another within the system, but which is simpler to operate and less expensive to manufacture than previous systems.

SUMMARY OF THE INVENTION

The present invention meets that need by providing a vial transport apparatus which is capable of storing and retrieving samples and then transporting them from one location in a sampling system to another without the complexity and expense of robotic arms or gripper elements. The present invention utilizes a passive hook arrangement to engage the vials for transport and can be operated using a standard three motor system for transport in the X, Y, and Z directions. Alternatively, the present invention may be used a two motor system operating only in the X and Z directions where a single row of vials is used. In another alternative embodiment, one motor may be used to rotate a circular array of vials to a position where a two motor transport system operating in the X and Z directions can transport individual vials. As used in this specification, the term "vial" is meant to be inclusive of any tube, container or vessel which holds, or is adapted to hold, a sample, reagent, diluting liquid, or the like. Reference to X, Y, and Z directions is conventional in this art and refers to the cartesian coordinate system of two horizontal (X, Y) and one vertical (Z) axes.

In accordance with one aspect of the present invention, a vial transport apparatus is provided comprising means for engaging a vial and drive means for moving the engaging means in at least the X and Z directions, and preferably also in the Y direction. The engaging means comprises means for supporting the vial from beneath the vial and means for at least partially surrounding the vial to entrap the vial during transport thereof.

In order to overcome any slight misalignment of the engaging means and vial, and to insure that the vial becomes seated within the engaging means, the transport apparatus also includes means for applying a downward force on the vial as it is engaged. The means for applying the downward force may comprise, for example, a weighted arm or a spring loaded arm which urges the vial into the engaging means. Conversely, when the vial is deposited at a desired location, including return of the vial to its original location, the means for applying the downward force to the vial ensures that the vial disengages properly from the engaging means.

In a preferred embodiment of the invention, the supporting means for engaging the vial comprises a hook having a base. The means for at least partially surrounding the vial ensure that the vial is securely engaged for transport. In one embodiment of the invention, such means comprise at least two prongs extend upwardly from the base of the hook. The prongs are preferably contoured to fit the exterior surface of the vial and trap the vial within the hook. The use of additional prongs around the vial adds stability to the transport apparatus. Alternatively, the means for at least partially surrounding the vial may comprise a hollow tube or collar which is located on the transport apparatus above the top of the vial. As the vial is raised from beneath by the engaging means, it passes into the tube or collar where it remains secured for stable transport.

The vial transport apparatus of the present invention may be incorporated into an apparatus for the storage and retrieval of vials in a chemical analysis system. The storage and retrieval apparatus includes a plurality of vials, means for storing the vials, and means for retrieving individual ones of the vials from the storing means. The storing means include a tray for supporting individual ones of the vials in a matrix. Again, as described in greater detail above, the retrieving means comprise means for engaging a vial and drive means for moving the engaging means in the X, Y, and Z directions.

In a preferred embodiment of the invention, the tray includes a base having a series of laterally extending support brackets, with adjacent pairs of the brackets supporting individual ones of the vials. The adjacent pairs of brackets form therebetween slots beneath each vial, with the width of the slots being sized to permit the passage of the retrieving means vertically therethrough. Preferably, the support brackets are arranged in a series of rows on the base. However, the support brackets may also be arranged in a circle about the periphery of the base if the system is designed to be operated using a combination of rotary and linear motions (R Theta mechanisms).

A preferred environment for the transport apparatus of the present invention is in a sampler mechanism for automatically taking samples from multiple vials containing samples for chemical preparation and/or analysis. The autosampler includes, in combination, a plurality of vials containing samples, means for storing the vials, a sampling station including a sampling needle for taking a sample from a vial and withdrawing the sample therefrom, and means for retrieving individual ones of the vials from the storing means and transporting it to the sampling station. The vials are preferably of the type which include septums closing the tops of the vials. The septums are pierceable by the sampling needle.

As described in greater detail above, the storing means include a tray for supporting individual ones of the vials in a matrix. The retrieving means comprise means for engaging a vial, the engaging means comprising means for supporting the vial from beneath the vial and means for at least partially surrounding the vial to entrap the vial during transport thereof, and drive means for moving the engaging means in the X, Y, and Z directions. The retrieving means include means for applying a downward force on the vial as it is retrieved from the storing means.

The present invention also includes a method of storing and retrieving vials containing fluid samples comprising the steps of providing a series of vials having septums closing their respective tops stored in a matrix, engaging a selected vial from beneath the vial and raising it from the matrix while at least partially surrounding the vial to stabilize it for transport, and transporting the vial to a sampling station having a sampling needle. At the sampling station, the vial is raised onto the sampling needle, piercing the septum, and a sample is withdrawn therefrom. The vial is then lowered from the sampling needle and returned to the matrix.

In a preferred embodiment, the matrix is a tray, the vials are supported on the tray, and the vials are engaged by a hook. The hook engages the vial by lifting it upwardly through a slot in the tray. A downward force is preferably applied to the vial as the vial is lifted upwardly to seat the vial in the hook and stabilize it for transport.

In another form of the invention, the vials may be transported to various work stations where sample preparation is performed. For example, the sample may be diluted prior to analysis. In addition, or alternatively, the sample may have a reagent added to it, and the sample mixed and/or heated prior to analysis. Thus, a preferred method for storing and retrieving vials containing fluid samples comprises the steps of providing a series of vials stored in a matrix, engaging a selected vial from beneath the vial and raising it from the matrix while at least partially surrounding the vial to stabilize it for transport, and moving the vial to a work station. The vial is then lowered into the work station and disengaged from the transport mechanism. At the work station, the sample may be diluted, or a reagent may be added. The sample may also be subjected to heating and/or mixing. After retrieving the vial from the work station, it is returned to the matrix.

In a preferred form of the invention, the matrix is a tray, the vials are supported on the tray, and the vials are engaged by a hook which transports the vials to the work station. Preferably, the hook engages a vial by lifting it upwardly through a slot in the tray. A downward force is applied to the vial as the vial is lifted upwardly to assure that the vial is seated on the hook and stabilized for transport.

Many prior art vial storage systems have no capability to transport or position the vials outside of the matrix in which they are stored. Rather, such systems rely upon movement of either the entire matrix, using two linear motions (X and Y directions) or combination of linear and rotary motion (R Theta mechanisms), or of the sampling needle. Further, such systems require a third motor to push the sampling needle through the septum covering the vials. Such systems are greatly limited in their ability to perform sample preparation functions such as shaking, mixing, or heating individual vials.

More expensive and complex robotics systems using active gripper mechanisms do have the capability to move an individual vial from its position in the matrix. However, the apparatus and method of the present invention provide this capability without resort to additional motors, robotic arms, or active grippers. The passive transport hook of the present invention provides for reliable individual sample vial movement to both sample preparation and needle sampling work stations. Further, the hook of the present invention, entraps individual vials securely at their bases. Active grippers used by some prior systems which grab the vials around their circumferences may slip up or down the vial interfering with sampling or sample preparation. Because of the design of the transport hook of the present invention, no slipping problems occur.

Accordingly, it is an object of the present invention to provide a vial transport apparatus which is capable of storing and retrieving samples and transporting them from one location in a sampling system to another without the complexity and expense of robotic arms or gripper elements. This, and other objects and advantages of the present invention will become apparent from the following detailed description, the accompanying drawings, and the appended claims.

Detailed Description of the Preferred Embodiments

While the vial transport apparatus of the present invention may find use in a number of environments, it will be described herein with respect to a preferred embodiment in conjunction with an automatic sampling system for chemical sample preparation and/or analysis. Further, the vial transport apparatus will Be described with reference to its preferred configuration in which it may be driven in the X, Y, and Z directions.

Figure 1:
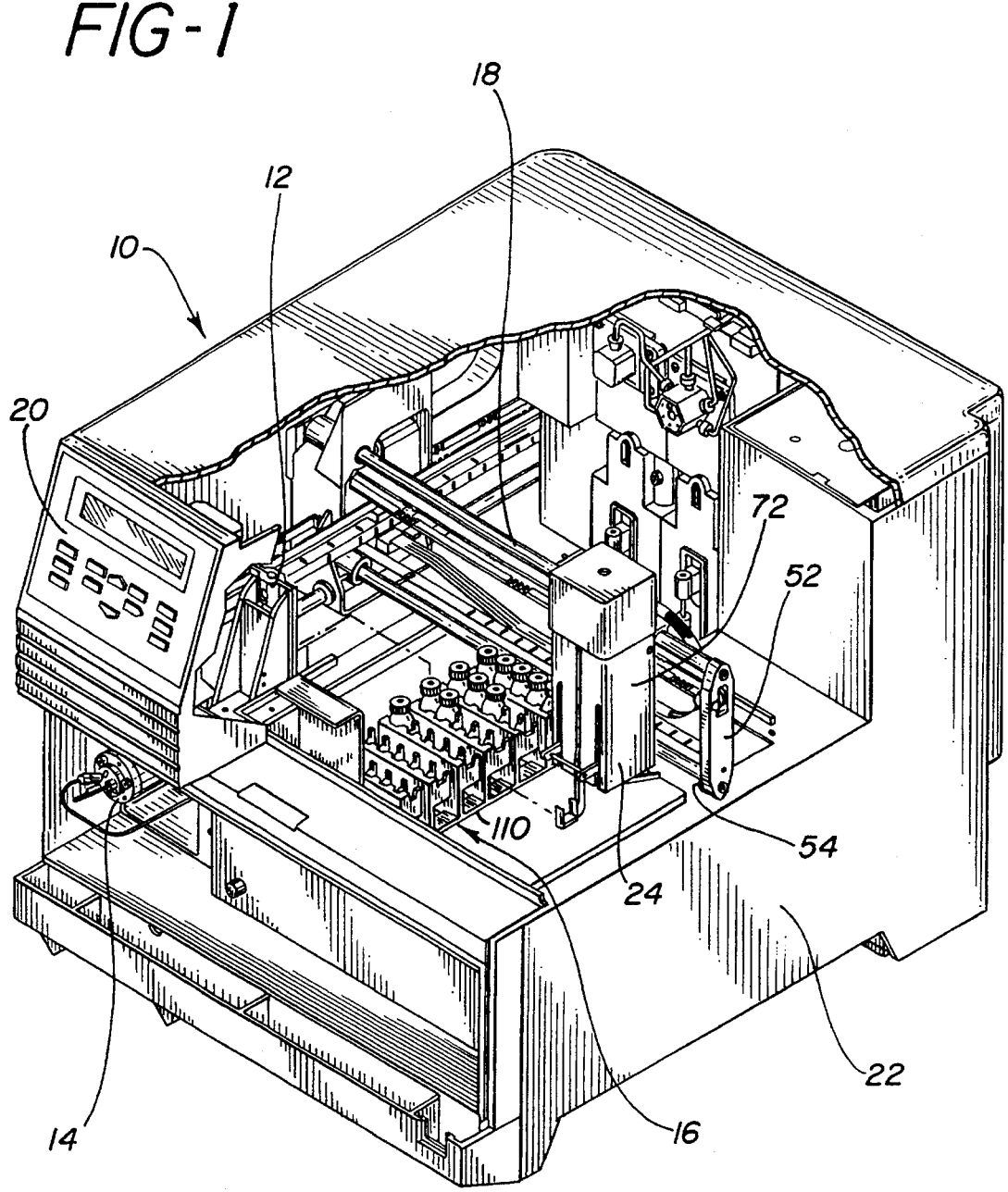
FIG. 1 is a perspective view of the transport mechanism of the present invention as used in an automatic sampling system.

Referring now to FIG. 1, a perspective view of the autosampler system 10 is shown with the transport hook and transport mechanism installed therein. While the invention is described in conjunction with an autosampler, it will be apparent to those skilled in the art that the transport hook and drive mechanism may find use in a number of systems which require retrieval and storage of multiple containers.

As shown, autosampler 10 includes a sampling station 12, an injector valve 14, vial storage tray 16, and vial transport apparatus 18. Autosampler 10 is designed to be operated automatically from a control panel 20 located on the front of housing 22 using a microprocessor to control the operation thereof in a manner generally known in the art.

Figure 6:
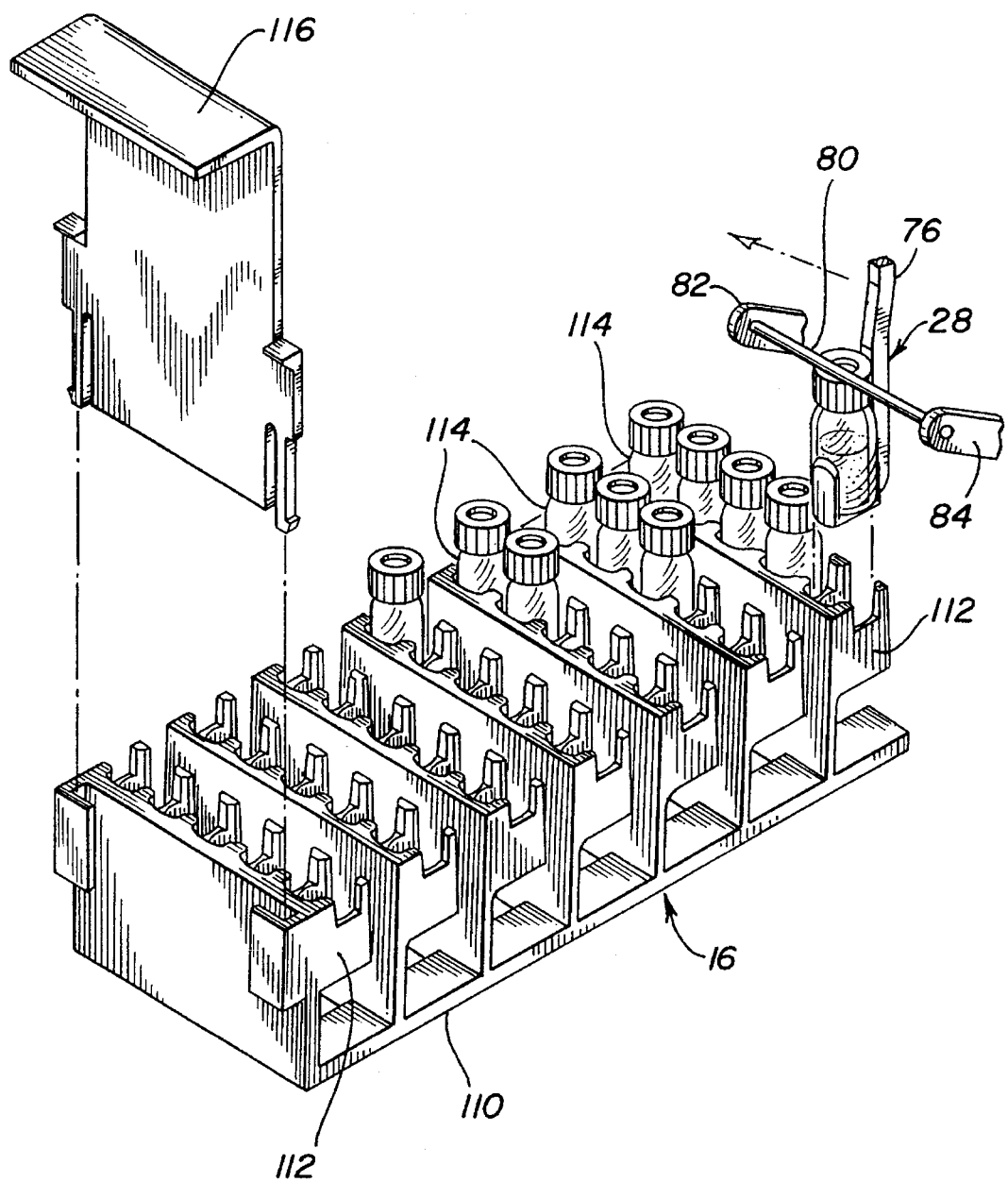
FIG. 6 is a perspective view of a tray containing sample vials adapted for use in the storage and retrieval system of the present invention.

Vial storage tray 16 is shown in greater detail in FIG. 6 and includes a base 110 having a series of laterally extending support brackets 112. A handle 116 provides a convenient gripping means for depositing storage tray 16 in autosampler 10 and removing it therefrom. While only a single storage tray is shown in FIG. 1, autosampler 10 may be sized to accommodate two or more trays.

Adjacent pairs of support brackets 112 support individual vials 114. Between each pair of brackets is a slot which is sized to permit the passage of hook 28 upwardly and downwardly therethrough as explained in greater detail below. While a preferred rectangular arrays of rows is shown in FIG. 6, it will be apparent to those skilled in the art that a different array configuration may be used such as a circular array such as that taught in Bradley et al, commonly-assigned U.S. Pat. No. 4,478,099, the disclosure of which is hereby incorporated by reference.

Figure 2:
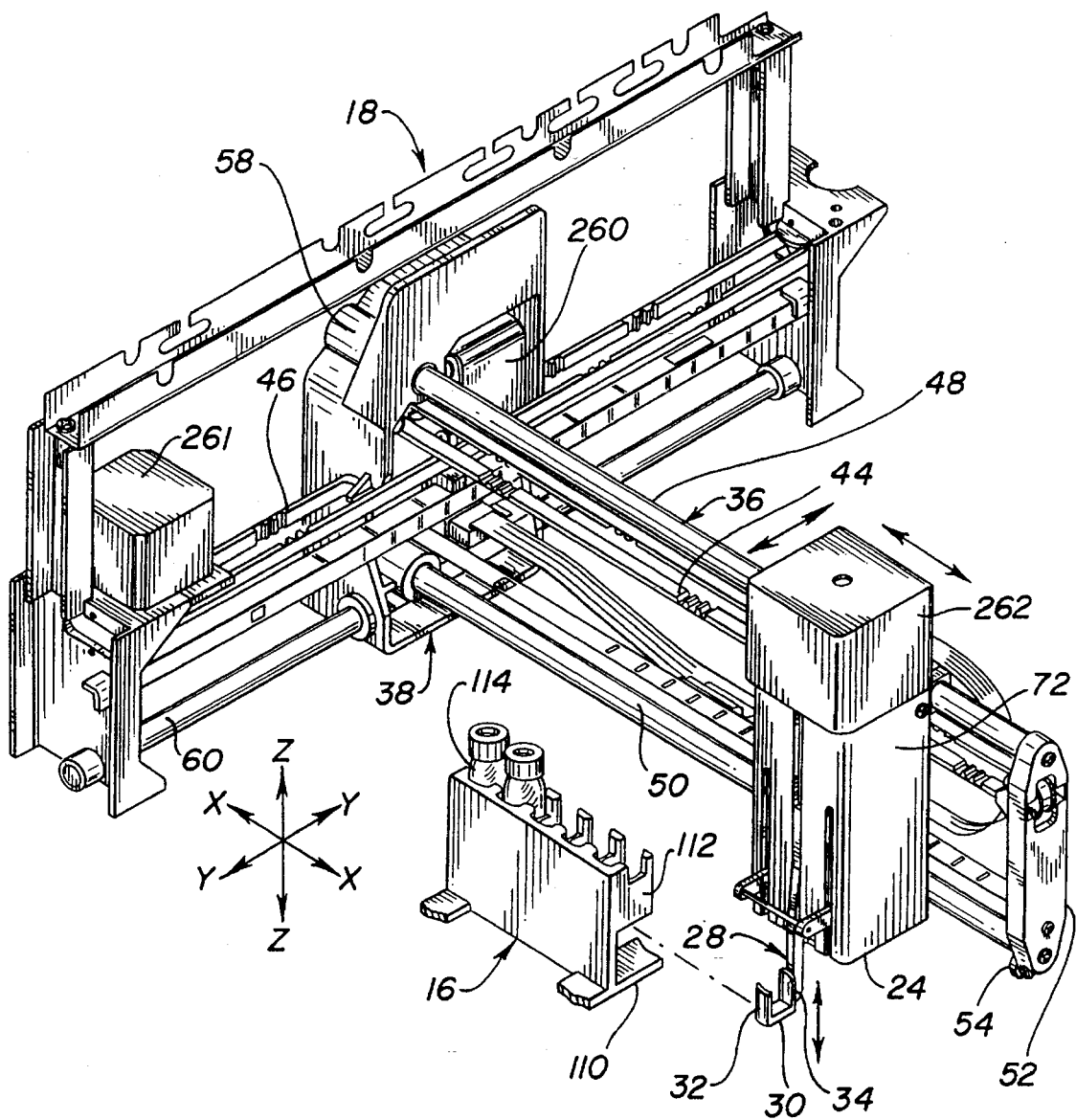
FIG. 2 is a perspective view of the X, Y, Z drives which move the transport hook from one location to another.

The vial transport apparatus 18 is shown in greater detail in FIG. 2 where the apparatus includes means 24 for engaging the vials and drive means 260, 261, and 262 for moving the engaging means 24 in the X, Y, and Z directions, respectively. The X, Y, and Z, directions are denoted by the arrows in FIG. 2. As shown, the engaging means 24 includes a passive hook 28 which is constructed to engage the vials from beneath and at least partially surround the vials. Hook 28 includes a base 30 and a pair of opposed, upstanding prongs 32, 34. As can be seen, prongs 32, 34 have a slight concave shape which is contoured to fit loosely around the exterior surface of the vials and entrap them within the hook for transport. While two upstanding prongs are shown, it will be apparent to those skilled in the art that additional prongs may be utilized for additional support of the vials if needed.

Vial transport apparatus 18 includes an X-direction carriage assembly 36 and a Y-direction carriage assembly 38. Each carriage assembly includes drive means 260 and 261, respectively, which may be a motor, such as an electric stepper motor. Each carriage assembly also includes timing belts 44 and 46, respectively, which permit precise control of the positioning and movement of hook 28. Additionally, the X-direction carriage assembly includes a pair of cylindrical rails 48 and 50 on which the vial engaging means 24 rides. To insure correct tracking in the X-direction, carriage assembly 36 also includes a flange 52 having a roller 54 which rides along a floor in housing 22 (shown in FIG. 1).

For movement in the Y-direction, carriage assembly 38 includes a mounting boss 58 into which cylindrical rails 48 and 50 are secured. Carriage assembly 38 rides along cylindrical rail 60 as driven by stepper motor 261 and timing belt 46. Both of the stepper motors are under the control of a microprocessor (not shown) which control the movement of the vial transport apparatus.

Figure 3:
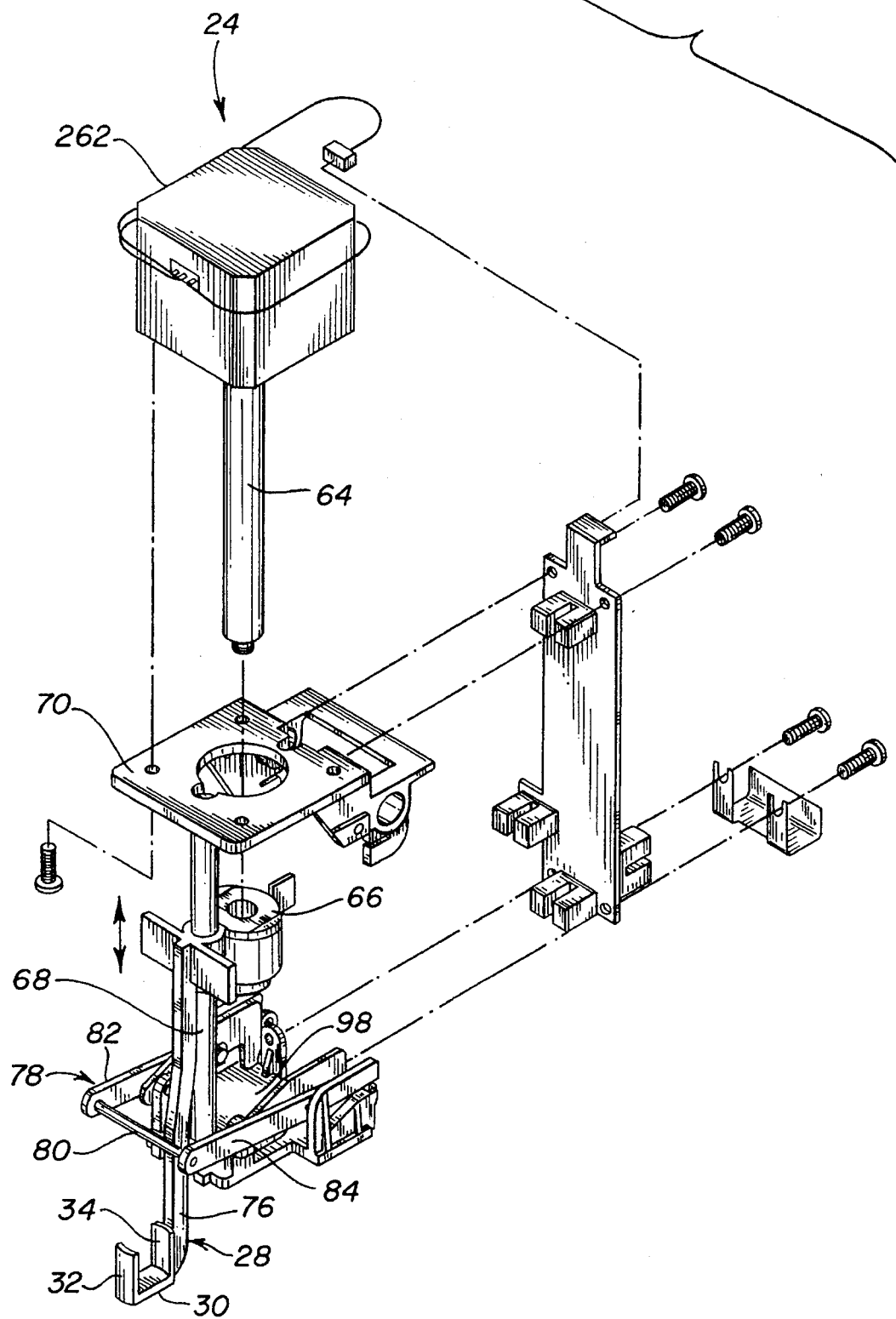
FIG. 3 is an exploded perspective view of the transport hook of the present invention.

Referring now to FIG. 3, vial engaging means 24 is shown in greater detail. Vial transport apparatus 18 includes a drive means 262 for movement of hook 28 in the Z-direction, such an electric stepper motor which is secured to the upper frame 70 of engaging means 24. As shown, stepper motor drive means 262 drives lead screw 64 which in turn is connected to hook nut 66. Rotation of the lead screw 64 causes hook nut 66, and hook 28 to which it is secured, to raise and lower. Vertical (Z-direction) movement of hook 28 is controlled by the hook sliding along rod 68 which is itself secured to upper frame 70 and lower frame 98. A cover 72, shown in FIGS. 1 and 2, is designed to fit over engaging means 24, protecting the moving parts therein.

Figure 4:
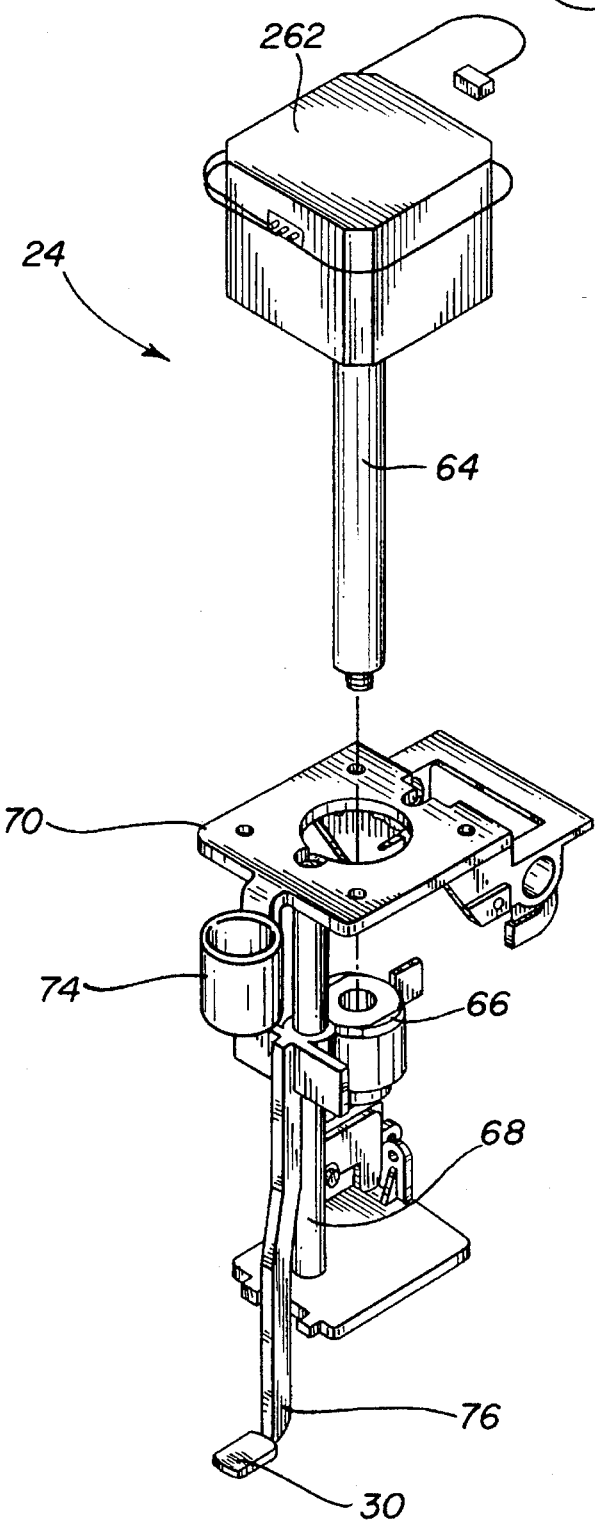
FIG. 4 is a perspective view of an alternative construction of the transport hook.

As previously described, hook 28 may include a base 30 and upstanding prongs 32 and 34. Alternatively, as shown in FIG. 4, a hollow tube or collar 74 may replace prongs 32, 34 and completely surrounds the vials during transport. Hollow tube 74 may be secured directly to upper frame 70 of engaging means 24. As the vial is removed from the tray, it is first stabilized by the tray and then in turn by hollow tube or collar 74. Once the vial is in the collar, it can be safely transported to other locations in the autosampler.

Figure 5:
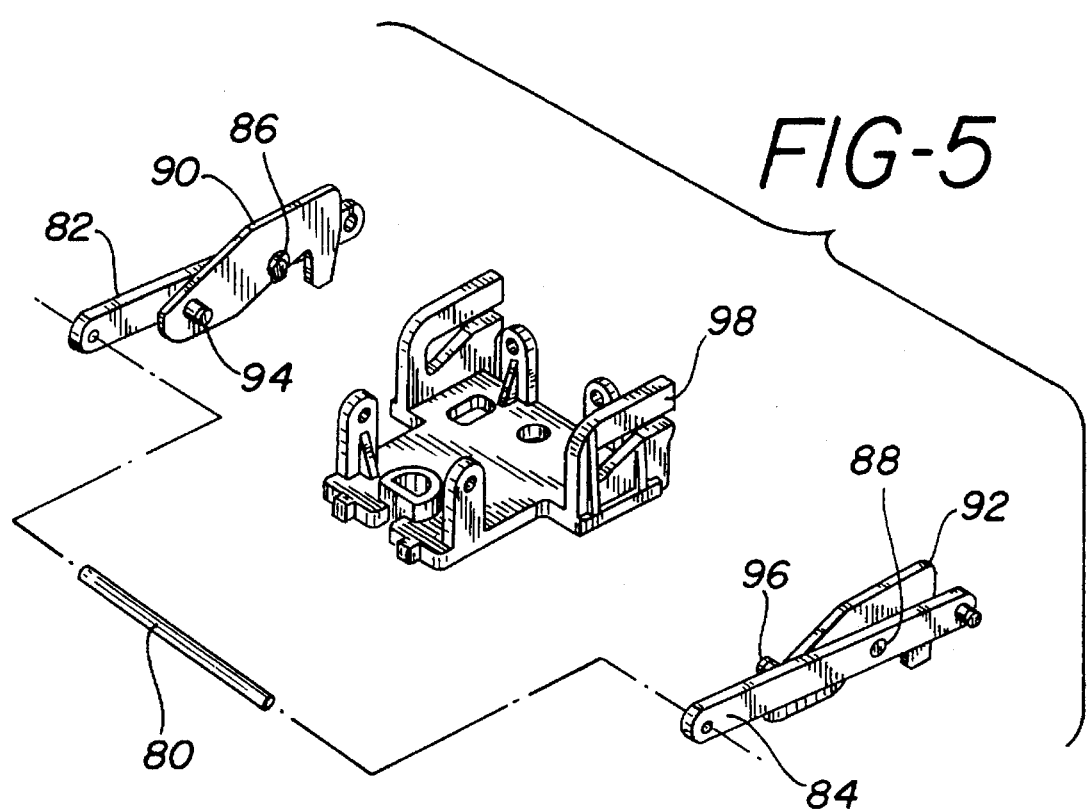
FIG. 5 is an exploded view of the weighted arm used in the transport hook.

In operation to overcome any slight misalignment of hook and vial, and to ensure that the vial is seated within vial transport apparatus 18, means 78 are provided for applying a downward force on the vial as it is engaged by hook 28. As shown in FIGS. 3 and 5, one preferred means is a weighted arm 80 which is designed to bear against the top of a vial as the vial is lifted by hook 28, see FIG. 6. The opposing ends of arm 80 are secured to links 82 and 84, which are in turn mounted by linkage pins 86, 88 to driver linkages 90 and 92, respectively. A second set of linkage pins 94, 96 secure links 82, 84 to lower frame 98 of vial transport apparatus 18.

In operation, vial transport apparatus 18 is moved to a predetermined position immediately beneath a vial in storage tray 16 by drive means 260 and 261. Stepper motor 262 is then activated to raise hook 28 through the slot formed between support brackets 112 as shown in FIG. 6. The base 30 and prongs 32, 34 of hook 28 engage the base of a vial 114 and continue to lift it vertically until the apparatus and vial clear the top of tray 16. Stepper motor drive means 260 and 261 are then actuated as required to cause the vial transport apparatus 18 to transport a vial 114 to, for example, sampling station 12. At sampling station 12, stepper motor 262 is again actuated to raise vial 114 against sampling needle 120 as explained in greater detail below and with reference to FIG. 7.

Once a sample has been taken from the vial at sampling station 12, stepper motor 62 is reversed, and vial 114 is lowered on hook 28. Stepper motor drive means 260 and 261 are then again actuated to transport the vial back to its proper position above a sot in storage tray 16. Actuation of stepper motor 262 then lowers the vial back into storage tray 16. Hook 28 fits between the slot formed by adjacent support brackets 112, and deposits vial 114 on the brackets.

In its preferred environment of an autosampler as illustrated, the transport apparatus of the present invention may be programmed to automatically take samples from multiple vials stored in a storage tray and transport them to a different location within the autosampler housing where various sample preparation, mixing, or heating steps may be carried out. For example, vial transport apparatus 18 may move a vial from storage tray 16 to a heater mixer device such as that disclosed in Nohl, commonly-assigned U.S. Pat. No. 5,044,428, the disclosure of which is hereby incorporated by reference. Likewise, a vial may be transported to a sample preparation chamber such as that taught by Nau et al in commonly-assigned U.S. Pat. No. 4,792,434, the disclosure of which is hereby incorporated by reference.

Figure 7:
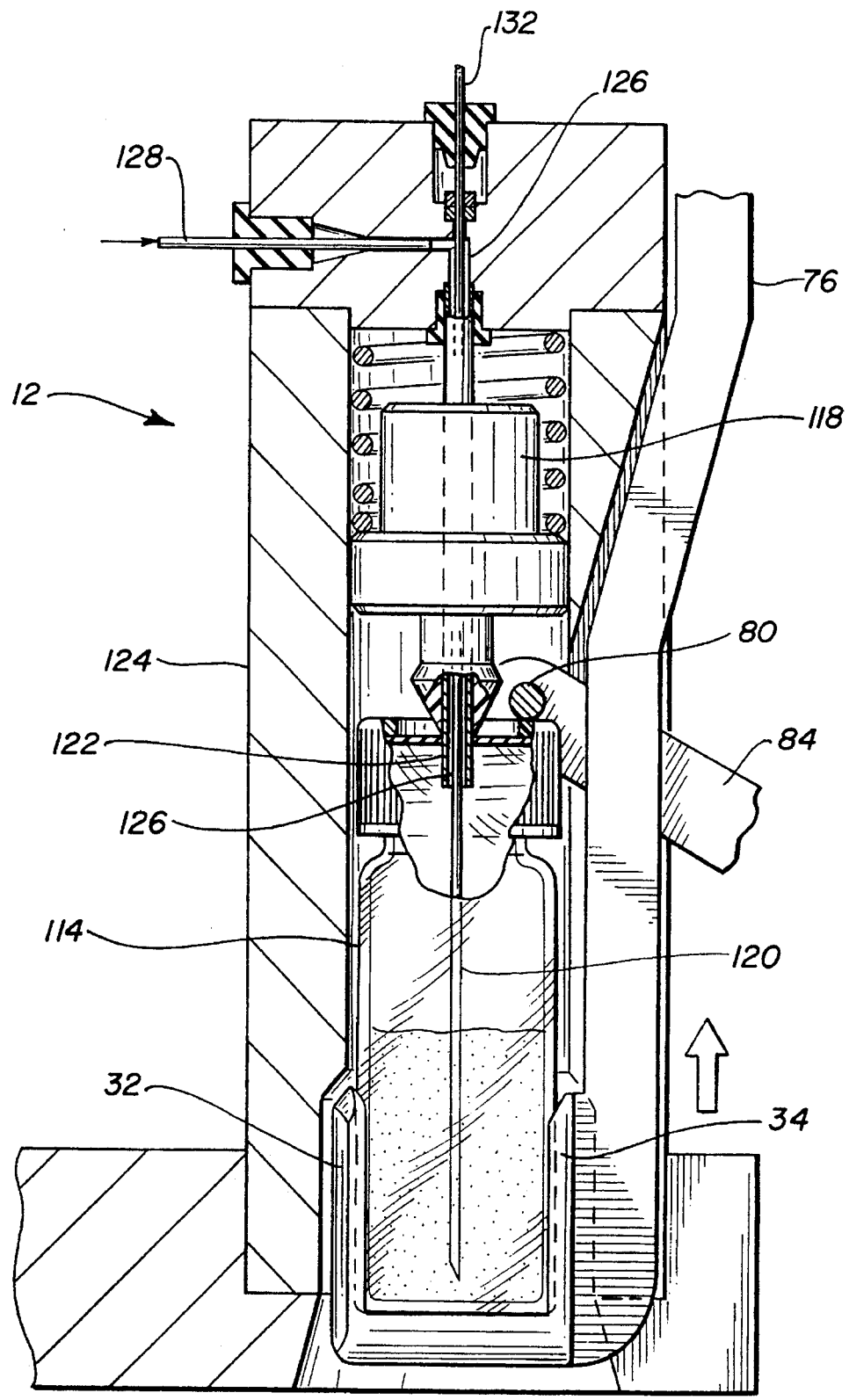
FIG. 7 is a cross-sectional view at the sampling station illustrating the transport hook lifting a vial onto a sampling needle.

In almost all instances, however, the samples in vials 114 will be transported either directly from storage tray 16, or from one of the other sample mixing, heating, or preparation stations to sampling station 12 where a sample is taken from the vial and analyzed. Sampling station 12 may be constructed as taught in Bradley et al, commonly-assigned U.S. Pat. No. 4,478,099. As best shown in FIG. 7, sampling station 12 includes a sampling needle assembly 118 which includes an inner, sample needle 120 and an outer venting needle 122 in block 124. Outer needle 122 is concentric with sampling needle 120 to provide an annular passageway 126 between the two needles. This vents the vial by allowing air to pass to annular passageway 126 through conduit 128.

Sampling needle 120 is longer than outer venting needle 122 so that the lower end of needle 120 extends downwardly below the surface of the liquid in vial 114 while the end of needle 122 remains above the surface of the liquid sample when the vial 114 has been lifted by hook 28 to the sampling position illustrated in FIG. 7. A sample line 132 is connected to the upper end of sampling needle 120. Alternatively, the sampling needle 120 may be a continuous piece which extends to injector valve 14.

The liquid sample in vial 114 is drawn up through the lower end of needle 120 by suction produced by a syringe (not shown). The sample in sample line 132 is then conducted through an injector valve 14, shown in FIG. 1, and on towards the syringe. Injector valve 14 may be a six port valve as taught by Nohl et al, commonly-assigned U.S. Pat. No. 4,957,009, the disclosure of which is hereby incorporated by reference. From injector valve 14, the sample is sent to an analysis device such as, for example, a liquid chromatograph (not shown).

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A vial transport apparatus comprising:

means for engaging a vial, said engaging means comprising means for supporting said vial from beneath said vial and means for at least partially surrounding said vial to entrap said vial during transport thereof; and drive means for moving said engaging means in at least the X and Z directions.

2. The vial transport apparatus of claim 1 including means for applying a downward force on said vial as it is engaged.

3. The vial transport apparatus of claim 2 in which said means for applying said downward force comprises a weighted arm.

4. The vial transport apparatus of claim 2 in which said means for applying said downward force comprises a spring loaded arm.

5. A vial transport apparatus comprising:

means for engaging a vial, said engaging means comprising means for supporting said vial from beneath said vial, said supporting means comprising a hook having a base and means for at least partially surrounding said vial to entrap said vial during transport thereof;

means for applying downward force on said vial as it is engaged; and drive means for moving said engaging means in at least the X and Z directions.

6. The vial transport apparatus of claim 5 in which said means for at least partially surrounding said vial comprises at least two prongs extending upwardly from said base of said hook.

7. The vial transport apparatus of claim 2 in which said means for at least partially surrounding said vial comprises a hollow collar.

8. Apparatus for the storage and retrieval of vials comprising:

a plurality of vials:

means for storing said vials, said storing means including a tray for supporting individual ones of said vials in a matrix; and means for retrieving individuals ones of said vials from said storing means, said retrieving means comprising means for engaging a vial, said engaging means comprising means for supporting said vial from beneath said vial and means for at least partially surrounding said vial to entrap said vial during transport thereof, and drive means for moving said engaging means in at least the X and Z directions.

9. The storage and retrieval apparatus of claim 8 in which said retrieving means include means for applying a downward force on said vial as it is retrieved from said storing means.

10. The storage and retrieval apparatus of claim 9 in which said means for applying said downward force comprises a weighted arm.

11. The storage and retrieval apparatus of claim 9 in which said means for applying said downward force comprises a spring loaded arm.

12. Apparatus for the storage and retrieval of vials comprising:

a plurality of vials;

means for storing said vials, said storing means including a tray for supporting individual ones of said vials in a matrix; and means for retrieving individual ones of said vials from said storing means, said retrieving means comprising means for engaging a vial, said engaging means comprising means for supporting said vial from beneath said vial, said supporting means comprising a hook having a base and means for at least partially surrounding said vial to entrap said vial during transport thereof, and drive means for moving said engaging means in at least the X and Z directions.

13. The storage and retrieval apparatus of claim 12 in which said means for at least partially surrounding said vial comprises at least two prongs extending upwardly from said base.

14. The storage and retrieval apparatus of claim 8 in which said means for at least partially surrounding said vial comprises a hollow collar.

15. The storage and retrieval apparatus of claim 8 in which said tray includes a base having a series of laterally extending support brackets, with adjacent pairs of said brackets supporting individual ones of said vials, said adjacent of brackets forming therebetween slots beneath each vial, the width of said slots being sized to permit the passage of said retrieving means vertically therethrough.

16. The storage and retrieval apparatus of claim 15 in which said support brackets are arranged in a series of rows on said base.

17. The storage and retrieval apparatus of claim 15 in which said support brackets are arranged in a circle about the periphery of said base.

18. A sampler mechanism for automatically taking samples from multiple vials containing samples for chemical preparation and/or analysis comprising:

a plurality of vials containing samples, said vials including septums closing the tops of said vials;

means for storing said vials, said storing means including a tray for supporting individual ones of said vials in a matrix;

a sampling station including a sampling needle for taking a sample from a vial by piercing said septum on said vial and withdrawing said sample therefrom; and means for retrieving individual ones of said vials from said storing means and transporting them to said sampling station, said retrieving means comprising means for engaging a vial, said engaging means comprising means for supporting said vial from beneath said vial and means for at least partially surrounding said vial to entrap said vial during transport thereof, and drive means for moving said engaging means in at least the X and Z directions.

19. The sampler mechanism of claim 18 in which said retrieving means include means for applying a downward force on said vial as it is retrieved from said storing means.

20. The sampler mechanism of claim 19 in which said means for applying said downward force comprises a weighted arm.

21. The sampler mechanism of claim 19 in which said means for applying said downward force comprises a spring loaded arm.

22. The sampler mechanism of claim 18 in which said supporting means comprises a hook having a base.

23. The sampler mechanism of claim 22 in which said means for at least partially surrounding said vial comprises at least two prongs extending upwardly from said base.

24. The sampler mechanism of claim 18 in which said means for at least partially surrounding said vial comprises a hollow collar.

25. The sampler mechanism of claim 18 in which said tray includes a base having a series of laterally extending support brackets, with adjacent pairs of said brackets supporting individual ones of said vials, said adjacent of brackets forming therebetween slots beneath each vial, the width of said slots being sized to permit the passage of said retrieving means vertically therethrough.

26. The sampler mechanism of claim 25 in which said support brackets are arranged in a series of rows on said base.

27. The sampler mechanism of claim 25 in which said support brackets are arranged in a circle about the periphery of said base.

\* \* \* \* \*